（12）United States Patent
Costovici

(10) Patent No.: US 8,414,520 B2
(45) Date of Patent: Apr. 9, 2013

(54) INSUFFLATION DEVICE WITH SECOND BYPASS FOR ADDITIONAL BODY CAVITY

(76) Inventor: Nicolas Anthony Costovici, Girona (ES)

( * ) Notice: Subject to any disclaimer, the term of this patent is extended or adjusted under 35 U.S.C. 154(b) by 322 days.

(21) Appl. No.: 12/725,221

(22) Filed: Mar. 16, 2010

(65) Prior Publication Data

US 2011/0118657 A1 May 19, 2011

(30) Foreign Application Priority Data

Nov. 18, 2009 (ES) .................................. 200931022

(51) Int. Cl.
*A61M 37/00* (2006.01)
(52) U.S. Cl. ......................................................... 604/26
(58) Field of Classification Search ..................... 604/23, 604/26
See application file for complete search history.

(56) References Cited

U.S. PATENT DOCUMENTS

| 5,006,109 A * | 4/1991 | Douglas et al. ................. 604/26 |
| 2006/0149170 A1 * | 7/2006 | Boynton et al. ................. 601/6 |
| 2009/0171268 A1 * | 7/2009 | Williams et al. ............... 604/26 |

* cited by examiner

Primary Examiner — Tatyana Zalukaeva
Assistant Examiner — Bradley Osinski
(74) Attorney, Agent, or Firm — Notaro, Michalos & Zaccaria P.C.

(57) ABSTRACT

A device comprising: a gas insufflation device (1), a first duct (2) for supplying gas to a member insertable (3) in a cavity of an individual, wherein the first duct (2) comprises a by-pass (21) for evacuating excess gas towards the exterior. The insertable member (3) has three passages and comprises a first mouth (31) at its rear end for coupling the first duct (2) to a passage (32) having an exit mouth (33), a second mouth (34) for coupling an effluent evacuation duct (5) to a passage (35) having an entrance mouth (36), and a third mouth (37) for connecting inflating means (6) of an expandable ring-shaped element (30) with a passage (38) having an exit mouth (39) to the expandable ring-shaped element (30) disposed before the mouths (33, 36).

7 Claims, 3 Drawing Sheets

INSUFFLATION DEVICE WITH SECOND BYPASS FOR ADDITIONAL BODY CAVITY

This invention claims priority to Spanish application No. 200931022 filed Nov. 18, 2009.

OBJECT OF THE INVENTION

The present invention relates to a device for insufflating gas and collecting effluents from the body cavities of an individual, preferably a device for rectal insufflation of gas for distending the intestines during the image-based exploration of said intestines.

BACKGROUND OF THE INVENTION

The present invention relates to a device that allows gas, for example air or carbon dioxide, to be introduced into the intestines of a patient in such a manner that these become distended, thereby enabling image-based diagnostic methods.

During said exploration, it is normal for an individual to expel or spill effluents from the rectal cavity towards the exterior, with the risk of contaminating the means used to insufflate said gas internally and the place where the exploration is being carried out.

A device that reduces these problems is known to exist, which comprises: a gas-insufflation device, a first duct for supplying gas provided by the insufflation device towards the interior of a body cavity of an individual; barriers inserted in the first duct for preventing the passage of effluents from the individual towards the interior of the insufflation device; a deposit for collecting said effluents; a member insertable in a cavity of the individual, attachable to the first duct and having an expandable ringed-shaped element for perimetrally sealing the cavity of the individual; and means for inflating the expandable ring-shaped element upon introducing the member insertable in a cavity of an individual.

In this manner, on inserting the insertable member in the rectal cavity of an individual, the effluents produced during the exploration pass through the first duct and are collected in the deposit. This device poses several problems, the main ones being that the first duct insufflates gas and collects effluents via the same passage, which contributes to the greater contamination of the insufflation device. Additionally, the insufflation device must support the excess pressure that may be produced during the diagnosis process, due to which it must absorb gases stemming from the cavity, becoming contaminated even if the barriers effectively prevent the passage of liquids and solids.

Additionally, total extraction of effluents is not achieved with these devices, as the current of insufflated gas hampers the collection of effluents circulating through the duct in the opposite direction, whereupon part of said effluents remain in the rectal cavity. The effluents remaining in the rectal cavity distort the images obtained by the radiologist during the image-based exploration, considerably hampering diagnosis.

DESCRIPTION OF THE INVENTION

The device for insufflating gas and collecting effluents from the body cavities of an individual that is the object of this invention has technical peculiarities destined for improving the patient's comfort and ensuring the cleanliness and hygiene of the gas insufflation device.

The device comprises: a gas insufflation device, a first duct for supplying the gas provided by the insufflation device towards the interior of a body cavity of an individual; barriers inserted in the first duct to prevent the passage of effluents from the individual towards the interior of the insufflation device; a deposit for collecting said effluents, a member insertable in a body cavity of the individual, attachable to the first duct and having an expandable ring-shaped element for perimetrally sealing the cavity of the individual; and means for inflating the expandable element upon introduction of the member insertable in a body cavity of an individual.

The first duct has a by-pass and a safety valve for automatically releasing the gas when the pressure of the gas contained in the first duct exceeds a pre-established value.

In accordance with the invention, the by-pass extends into a second gas evacuation duct when the pressure of the gas contained in the first duct exceeds a pre-established value.

This deviation of gas towards the exterior allows the excess gas in the cavity to be evacuated without entering the insufflation device, avoiding contamination thereof by the gases returning from the rectal cavity of the individual. It also facilitates control of the internal pressure of the cavity by allowing the gases to be directly released towards the exterior, maintaining the volume and pressure in the patient's cavity more constant.

Additionally, the second gas evacuation duct of the invention enables gas to be released outside of the area of operation of the medical personnel, avoiding contamination thereof and providing improved sanitary and hygienic conditions with regard to those devices and apparatuses wherein the safety valve is mounted directly or adjacent to the first duct.

In turn, the insertable member comprises a first mouth at its rear end for coupling the first duct to a first inner passage having an exit mouth disposed next to the front end of the insertable member, a second mouth for coupling an effluent evacuation duct to a second inner passage, having an exit mouth disposed next to the front end of the insertable member and a third mouth for connecting the inflating means of the expandable ring-shaped element with a third inner passage, having an exit mouth disposed inside the expandable ring-shaped element. This allows the gas supply to be insufflated into the cavity of an individual via a passage that is totally independent of the effluent collection route or path, which is collected via another independent passage, thereby reducing the possibility of contaminating the insufflation device with said collected effluents.

The insufflation device insufflates gas on a practically constant basis and said flow of gas to the patient prevents the liquids and effluents inside the rectum and colon from entering the first duct.

As the device allows gas to enter via one passage and the effluents to be collected via a different passage, said effluents are more effectively eliminated. This facilitates the work of the radiologist who is carrying out the diagnostic process as it does not distort the image obtained by said effluents, which are adequately collected.

The first duct has a second by-pass disposed in the section comprised between the connection by-pass of the second duct and the end connected to the insufflation device, to which a tube is connected for introducing gas in a cavity of the patient through the mouth or nose. Therefore, during gastrointestinal diagnosis, it is possible to distend the small intestine by means of said tube using a single insufflation device, balancing the internal pressure that distends both intestines from their two ends.

In a first embodiment, the length of the effluent evacuation duct, connected to the second mouth of the insertable member, is sufficient for collecting the effluents produced. However, it has been envisaged that for certain situations, the effluent evacuation duct, connected to the second mouth of the insertable member, is connected by its rear end to an effluent collection recipient when these are abundant.

The second duct, for gas evacuation, comprises scented barriers that eliminate the foul odour of the return gases evacuated towards the exterior.

The gas insufflation device comprises means for heating the gas to be supplied. These gas heating means comprise a thermostat that regulates the heating of the gas at a temperature of around 37.5° C., in such a manner that the gas introduced in the cavities of the individual is at the same temperature as his/her body temperature, rather than at the normally low temperature of decompressed bottled gas, for example. In this manner, the patient's comfort is enhanced and tension reduced.

At least one of the barriers disposed in the first duct comprises antiviral or antibacterial materials, in such a manner that the gas evacuated towards the exterior is cleaner. Likewise, at least one of the barriers comprises a hydrophobic filter that prevents said gas evacuated towards the exterior from having any humidity or water-related contaminant, in addition to increasing the safety and hygiene of the insufflation device.

The device has been envisaged to comprise clamping means, a clamp or blocking means disposed in the first duct before the barriers and in the evacuation duct, in such a manner as to prevent spilling the effluents after making the diagnosis on withdrawing and discarding single-use means.

DESCRIPTION OF THE FIGURES

In order to complement this description and for the purpose of further explaining the characteristics of the invention, a set of drawings has been included with this specification, wherein the following figures have been represented in an illustrative and non-limiting manner.

PREFERRED EMBODIMENT OF THE INVENTION

Figure 1:
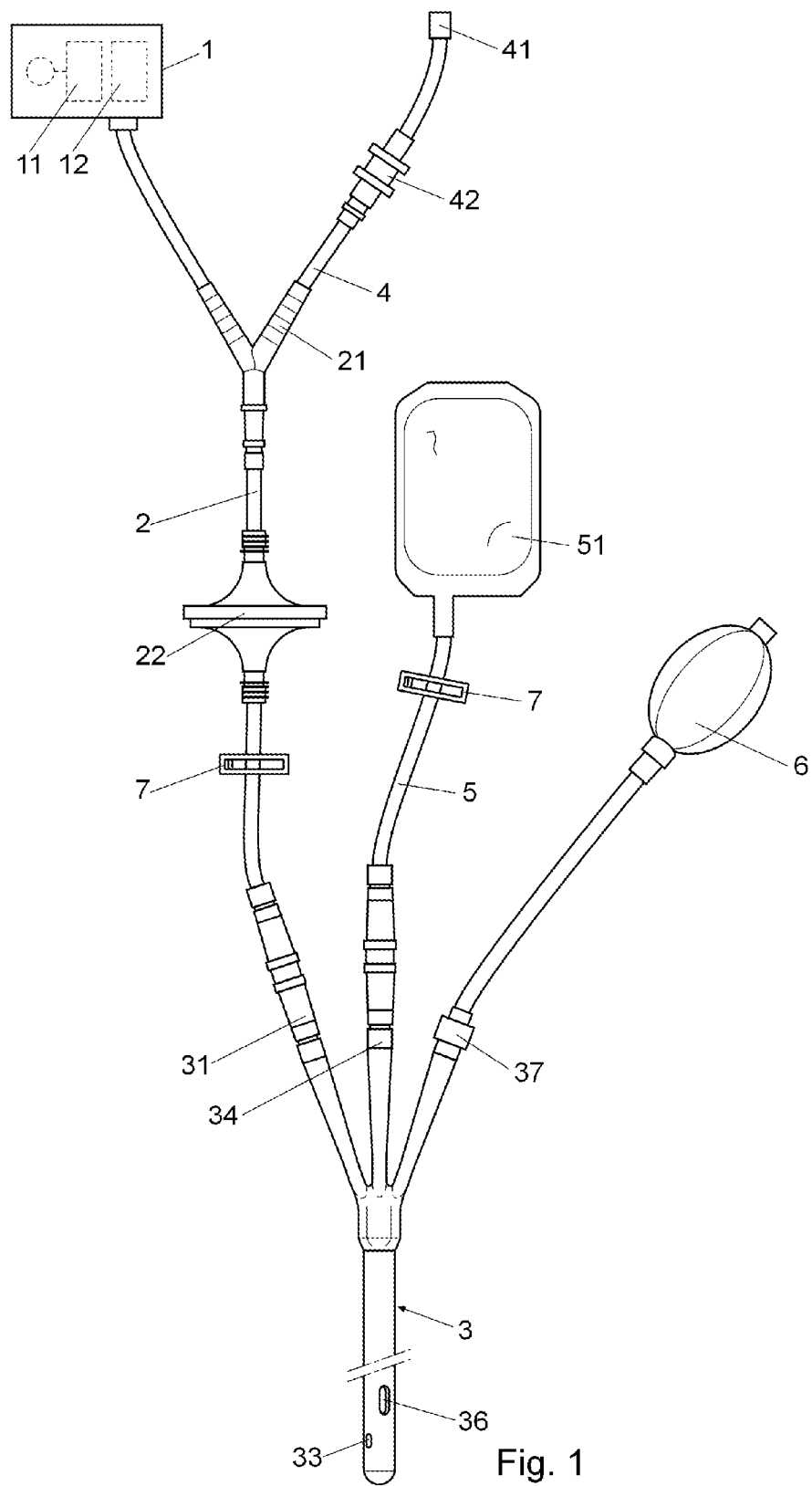
FIG. 1 shows a plan view of the device.
Figure 2:
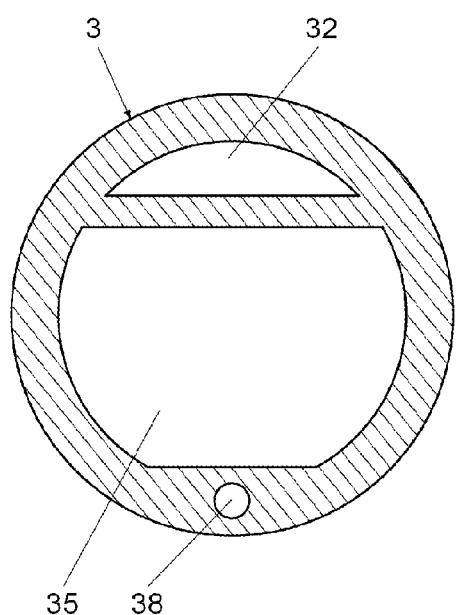
FIG. 2 shows a cross-section of the insertable member.
Figure 3:
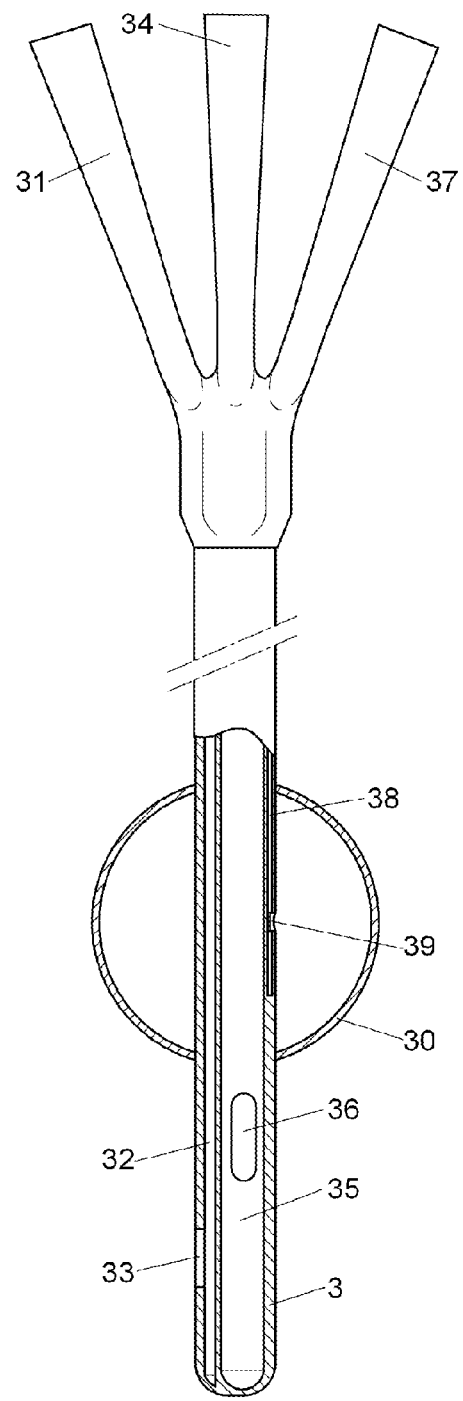
FIG. 3 shows a longitudinal section of the insertable member.

As can be observed in the aforementioned figures, the device for insufflating gas and collecting effluents from the body cavities of an individual comprises a first gas insufflation device (1) connected to a first duct (2) for supplying gas to the cavity of an individual through an insertable member (3), wherein the insufflation device (1) has gas heating means (11) and a thermostat (12) adjusted to supply gas at approximately 37.5° C.

The first duct (2) comprises a by-pass (21) next to the end connected to the insufflation device (1), said by-pass (21) being connected to a second gas evacuation duct (4) having a safety valve (41) for automatically releasing the gas towards the exterior when the pressure of the gas contained in the first duct (2) exceeds a pre-established value. A scented barrier (42) is disposed in said second duct (4) to avoid foul odours during gas evacuation.

The first duct (2) has, at (22), antiviral and antibacterial barriers and a hydrophobic filter disposed after the by-pass (21).

The insertable member (3) comprises a first mouth (31) at its rear end for coupling the first duct (2), by its free end, to a first inner passage (32) having an exit mouth (33) disposed next to the front end of said insertable member (3). The insertable member (3) also comprises a second mouth (34) for coupling an effluent evacuation duct (5) to a second inner passage (35) having an entrance mouth (36) disposed next to the front end of the insertable member (3). In turn, the insertable member (3) comprises a third mouth (37) for connecting inflating means (6) with a third inner passage (38) having an exit mouth (39) disposed inside an expandable ring-shaped element (30), said expandable ring-shaped element (30) being disposed around the insertable member (3) in order to block the entrance to the cavity by inflation thereof. This insertable member (3) has a rounded front end to facilitate its insertion into the rectal cavity without causing injury or discomfort.

The evacuation duct (5) has sufficient length for storing the effluents until they are discarded.

In one embodiment, an effluent collection recipient (51) having greater capacity is disposed at the end of this evacuation duct (5).

In one embodiment, clamps (7) have been coupled to the first duct (2) and the effluent evacuation duct (5) for shutting it off once used, thereby avoiding spilling the effluents and possible contamination on withdrawing the insertable member (3) from the cavity of the individual.

Figure 4:
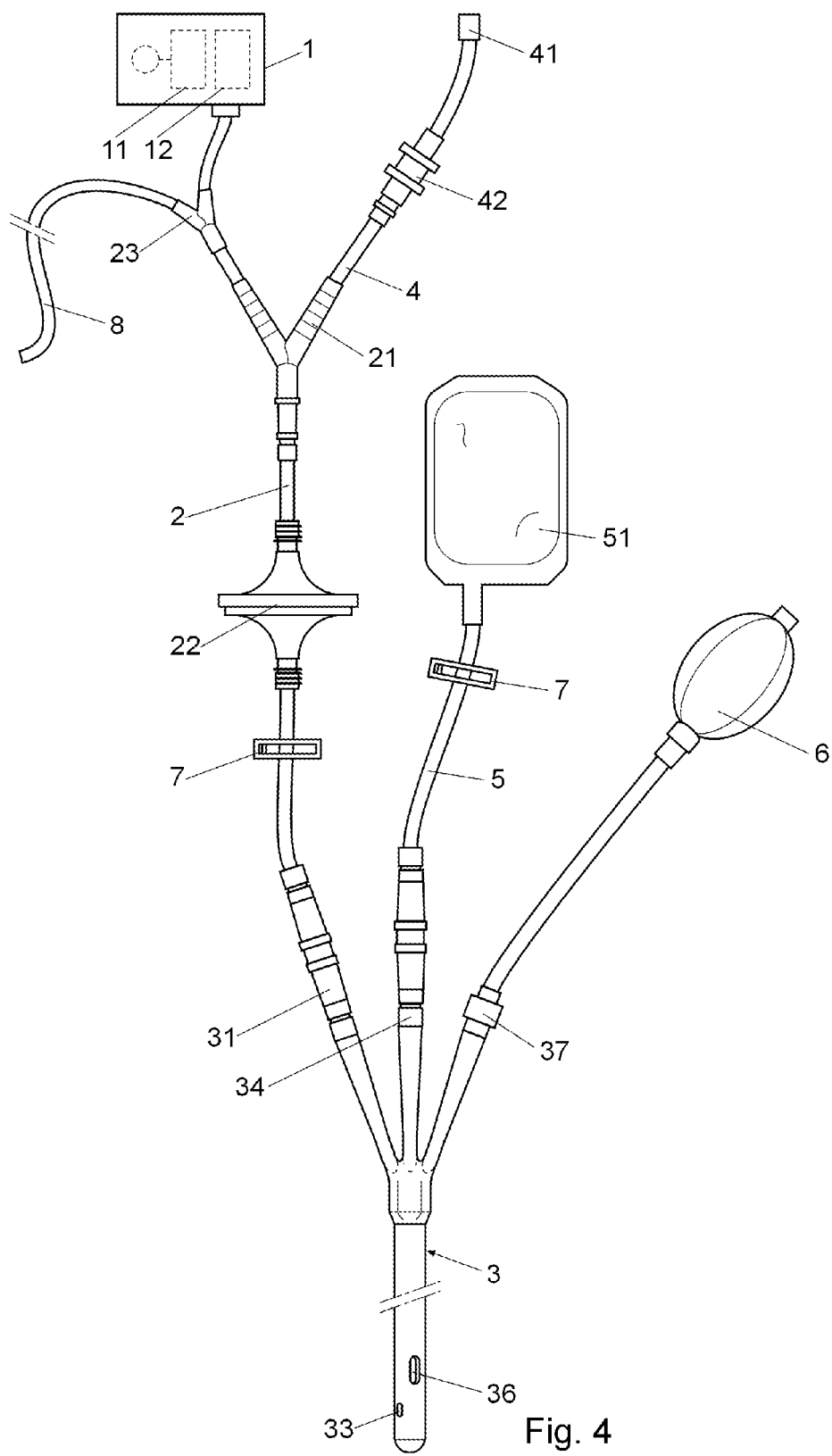
FIG. 4 shows a plan view of the device in a configuration with the second tube for introduction thereof through the nose or mouth.

In one embodiment, represented in FIG. 4, the first duct (2) has, in the section comprised between the by-pass (21) connecting the second duct (4) and the end connected to the insufflation device (1), a second by-pass (23) to which a tube (8) is connected for introducing gas in a cavity of the patient through the mouth or nose.

Having sufficiently described the nature of the invention, in addition to an example of preferred embodiment, we hereby state for the appropriate purposes that the materials, shapes, size and layout of the elements described may be modified, provided that said modification does not alter the essential characteristics of the invention, which are claimed below.

The invention claimed is:

1. A device for insufflating gas and collecting effluents from body cavities of an individual, the device comprising:
   a gas insufflation device (1);
   a first duct (2) for supplying the gas provided by the insufflation device (1) towards the interior of a body cavity of an individual;
   barriers (22) inserted in the first duct (2) to avoid the passage of effluents from an individual towards the interior of the insufflation device (1);
   an effluent collection recipient (51) for collecting said effluents;
   a member (3) insertable in a cavity of an individual, attachable to the first duct (2) and having an expandable ring-shaped element (30) for perimetrally sealing the cavity of the individual; and
   inflating means (6) for inflating the expandable ring-shaped element (30) upon introduction of the insertable member (3) in the body cavity of an individual;
   the first duct (2) having a by-pass (21) to which a second gas evacuation duct (4) is connected, having a safety valve (41) for automatically releasing gas from the first duct (2) when the pressure of the gas contained in the first duct (2) exceeds a pre-established value;
   the by-pass (21) being disposed in a section comprised between the insufflation device (1) and the barrier (22) that block passage of the effluents toward said insufflation device (1);

the insertable member (3) comprising a first mouth (31) at a rear end thereof that is toward the first duct (2) for coupling the first duct (2) for supplying gas to the individual and to a first inner passage (32) having an exit mouth (33) disposed next to a front end of the insertable member (3), a second mouth (34) for coupling an effluent evacuation duct (5) to a second inner passage (35) having an exit mouth (36) disposed next to the front end of the insertable member (3), said effluent evacuation duct (5) being connected at a rear end thereof to the recipient (51); and a third mouth (37) for connecting the inflating means (6) of the expandable ring-shaped element (30) with a third inner passage (38), having an exit mouth (39) disposed inside the expandable ring-shaped element (30);

wherein the first duct (2) has, in the section comprised between the by-pass (21) connecting the second duct (4) and the end connected to the insufflation device (1), a second by-pass (23) to which a tube (8) is connected for introducing gas in a cavity of the patient through the mouth or nose.

2. The device according to claim 1, wherein the second gas evacuation duct (4) comprises scented barriers (42).

3. The device according to claim 1, wherein the gas insufflation device (1) comprises means for heating (11) the gas to be supplied.

4. The device according to claim 3, wherein the gas heating means (11) comprise a thermostat (12) that regulates the heating of the gas at a temperature of around 37.5° C.

5. The device according to claim 1, wherein at least one of the barriers (22) disposed in the first duct (2) comprises antiviral or antibacterial materials.

6. The device according to claim 1, wherein at least one of the barriers (22) comprises a hydrophobic filter.

7. The device according to claim 1, further including clamping means, a clamp (7) or blocking means disposed in the first duct (2) before the barriers (22) and in the evacuation duct (5).

* * * * *